(12) United States Patent
Weber (10) Patent No.: US 9,724,030 B2
(45) Date of Patent: Aug. 8, 2017

(54) FLUID HANDLING DEVICE HAVING A SPRING MECHANISM

(71) Applicant: Smiths Medical Deutschland GmbH, Grasbrunn (DE)

(72) Inventor: Joerg Weber, Edling (DE)

(73) Assignee: Smiths Medical Deutschland GmbH, Grasbrunn (DE)

( * ) Notice: Subject to any disclaimer, the term of this patent is extended or adjusted under 35 U.S.C. 154(b) by 430 days.

(21) Appl. No.: 14/066,596

(22) Filed: Oct. 29, 2013

(65) Prior Publication Data

US 2014/0058287 A1 Feb. 27, 2014

Related U.S. Application Data

(63) Continuation of application No. PCT/EP2012/057805, filed on Apr. 27, 2012.

(30) Foreign Application Priority Data

Apr. 29, 2011 (DE) .................. 10 2011 075 028

(51) Int. Cl.
*A61B 5/15* (2006.01)
*A61B 5/155* (2006.01)
(Continued)

(52) U.S. Cl.
CPC ...... *A61B 5/150244* (2013.01); *A61B 5/1405* (2013.01); *A61B 5/1427* (2013.01);
(Continued)

(58) Field of Classification Search
CPC ................ A61B 5/1405; A61B 5/1427; A61B 5/150236; A61B 5/150244;
(Continued)

(56) References Cited

U.S. PATENT DOCUMENTS 3,680,985 A * 8/1972 Ginsberg .................. F04B 7/04
417/489
4,236,516 A 12/1980 Nilson
(Continued)

FOREIGN PATENT DOCUMENTS

CN 1802183 A 7/2006
DE 29713743 11/1997
(Continued)

*Primary Examiner* — Sean Dougherty
(74) *Attorney, Agent, or Firm* — Michael A. Glenn; Perkins Coie LLP (57) ABSTRACT

A fluid handling device includes a receiving container with a piston arranged therein in a displaceable manner, such that the volume of a fluid receiving reservoir may be changed by a displacement of the piston. In addition, the fluid handling device includes an actuation mechanism configured to displace a carrier bearing upon actuation of the former. Finally, the fluid handling device includes a spring mechanism configured to transfer a force from the carrier bearing to the piston so as to effect, in response to displacement of the carrier bearing in a first direction, a displacement of the piston within the receiving container such that a volume of the fluid reservoir is increased.

16 Claims, 8 Drawing Sheets

(51) Int. Cl.
*A61M 5/31* (2006.01)
*A61M 5/48* (2006.01)

(52) U.S. Cl.
CPC .. *A61B 5/150213* (2013.01); *A61B 5/150236* (2013.01); *A61B 5/150274* (2013.01); *A61B 5/150946* (2013.01); *A61B 5/150992* (2013.01); *A61B 5/155* (2013.01); *A61B 5/150328* (2013.01); *A61M 5/3148* (2013.01); *A61M 5/488* (2013.01)

(58) Field of Classification Search
CPC ............. A61B 5/150992; A61B 5/155; A61M 5/3155; A61M 5/31551; A61M 5/31563; A61M 5/31583; A61M 5/31586; A61M 5/14216–5/1422; A61M 5/1452; A61M 5/14546; A61M 5/31515
See application file for complete search history.

(56) References Cited

U.S. PATENT DOCUMENTS

| | | | | |
|---|---|---|---|---|
| 4,312,344 | A * | 1/1982 | Nilson | A61M 5/2425 604/212 |
| 4,325,369 | A | 4/1982 | Nilson | |
| 5,374,401 | A * | 12/1994 | von Berg | A61B 5/1405 422/534 |
| 5,961,472 | A * | 10/1999 | Swendson | A61M 5/3148 600/573 |
| 6,213,981 | B1 * | 4/2001 | Hiejima | A61M 5/1424 604/132 |
| 6,364,847 | B1 | 4/2002 | Shulze et al. | |
| 7,559,530 | B2 * | 7/2009 | Korogi | A61B 5/15003 251/149.6 |
| 8,491,537 | B2 * | 7/2013 | Kosinski | A61M 5/31511 604/187 |
| 2004/0124389 | A1 | 7/2004 | Phillips | |
| 2004/0216743 | A1 * | 11/2004 | Orr | A61M 16/0045 128/205.12 |
| 2006/0247582 | A1 * | 11/2006 | Alheidt | A61M 25/1018 604/228 |
| 2007/0179452 | A1 * | 8/2007 | Kosinski | A61M 5/31511 604/218 |
| 2008/0045862 | A1 * | 2/2008 | Dalebout | A61B 5/1411 600/573 |
| 2008/0255473 | A1 | 10/2008 | Dalebout et al. | |
| 2009/0030401 | A1 | 1/2009 | Phillips | |

FOREIGN PATENT DOCUMENTS

| | | |
|---|---|---|
| DE | 102005003516 | 4/2006 |
| EP | 0575917 | 12/1993 |
| JP | S52-135595 A | 11/1977 |
| JP | H02-186240 A | 7/1990 |
| WO | WO-97/18748 | 5/1997 |
| WO | WO-01/24707 | 4/2001 |
| WO | 2005/084548 A1 | 9/2005 |

* cited by examiner

FLUID HANDLING DEVICE HAVING A SPRING MECHANISM

CROSS-REFERENCE TO RELATED APPLICATIONS

This application is a continuation of copending International Application No. PCT/EP2012/057805, filed Apr. 27, 2012, which is incorporated herein by reference in its entirety, and additionally claims priority from German Application No. 10 2011 075 028.2, filed Apr. 29, 2011, which is also incorporated herein by reference in its entirety.

The present invention relates to the technical field of fluid handling, and in particular, the present invention relates to a fluid handling device which may be used as a blood sampling device in medical technology.

BACKGROUND OF THE INVENTION

For drip infusion or direct blood pressure measurement, an infusion line or a catheter is usually inserted into a patient's vein or artery so as to sample blood, for example for examination purposes, from an externally accessible location of the infusion line. To this end, for example, taps or, in relatively recent systems, sampling sites may be provided which communicate with an interior lumen of the infusion system and are accessible from outside by means of a hypodermic syringe.

Before blood can be sampled from this system, one should first of all ensure that only undiluted blood of the patient without any constituents of infusion solutions or anticoagulants are located in the area of the sampling site and/or at the tap, said anticoagulants being supplied, for example, in direct blood pressure measurement to prevent coagulation of the blood. To this end, for example, WO 88/01846 A1 envisages two sampling sites; the sampling site located closer to the patient serves to actually draw the blood sample. The sampling site located further away from the patient serves to temporarily remove infusion solutions from the system so that only undiluted blood will be present at the upstream sampling site. WO 88/01846 A1 thus offers an improved possibility of blood sampling as compared to an approach wherein a sodium chloride solution and mixed blood is initially drawn at a tap by using a syringe until pure blood can be sampled at the tap. Subsequently, blood for laboratory analysis (e.g. for examining blood gases, etc.) is sampled at this tap by means of a second syringe. The initially drawn amount of infusion solution and blood should not be recirculated to the patient since, due to the syringe aspiration process, blood cells are damaged and contamination of the blood may occur. When blood sampling is performed frequently, this drawing of mixed blood prior to each blood sampling without subsequent recirculation leads to a noticeable loss of liquid.

In the implementation according to WO 88/01846 it is suggested, despite the risk of contamination and cell damage, to recirculate the amount which has been drawn at the downstream sampling site by means of a conventional syringe, the needle of which penetrates a sealing plug which is otherwise tight, to the system. However, this involves extensive handling and involves the risk—in addition to the risk that contaminants, germs and other pathogens are introduced into the system—that the hospital personnel might be injured and infected by the needle while removing same, which has already led to AIDS or hepatitis infections in hospital personnel before.

It has therefore been proposed to use a system which is closed in that the downstream sampling site is configured as a temporary storage which is integrated in the pressure measurement or catheter system and has a piston/cylinder arrangement no longer accessible from outside, as is reported, for example, in the introduction to the description of EP 0575917 A2. However, with said blood sampling device, the problem arises that the temporary storage is not fully emptied in the event of reinfusion of the patient's blood, so that residual blood will coagulate there. If the above-mentioned processes are performed several times, it may therefore occur that coagulated residual blood returns to the patient's blood circulation from the temporary storage and highly endangers said patient.

Therefore, EP 0575917 A2 proposes a conical piston tip in connection with a conical cylinder space tip, the cone angle of the piston tip being larger than that of the cylinder space tip so as to ensure complete emptying during squeezing out. However, it becomes apparent that even with such a provision within a closed blood sampling system attached to a patient over a relatively long period (e.g. several days), it cannot be ensured that the inner space of the blood sampling system, in particular of the temporary storage, is not contaminated by introduced germs. Such introduction of germs may occur, for example, when the piston is actuated several times.

In addition, conventional approaches to blood sampling by means of a temporary storage have the disadvantage that in many cases it cannot be ensured that blood and/or infusion solution is not aspirated out of the patient and/or the pressure measurement line at too high a negative pressure. Too high a negative pressure caused by, e.g., excessive pulling of the piston may result in that degassing occurs which involves corresponding bubble formation taking place in the blood, and that the blood-vessel wall collapses and/or that vascular obstruction occurs, which may result in necrotizing of tissue right up to a patient's death, depending on the arterial sampling site in the patient.

Even though excessive negative pressure formation may be prevented by appropriately cautious handling on the part of the hospital personnel when manipulating the temporary reservoir, this involves a correspondingly high standard of training and knowledge on the part of the personnel. Notwithstanding the above, the process involves a large amount of time on account of the care that is taken.

Finally, a temporary storage of a closed blood system makes sterilization by means of, e.g., ETO gas more difficult in a state wherein the temporary storage is in a state in which it is assembled and already arranged, e.g., in a gas-permeable packaging.

SUMMARY

According to an embodiment, a fluid handling device may have: a receiving container with a piston arranged therein in a displaceable manner, such that the volume of a fluid receiving reservoir may be changed by a displacement of the piston; an actuation mechanism configured to displace a carrier bearing upon actuation of the former; and a spring mechanism configured to transfer a force from the carrier bearing to the piston so as to effect, in response to displacement of the carrier bearing in a first direction, a displacement of the piston within the receiving container such that a volume of the fluid reservoir is increased, the actuation mechanism including a rotary knob with a thread mechanism, the carrier bearing being mounted on a thread element including a thread, the thread mechanism engaging with the thread of the thread element so that the displacement of the carrier bearing may be effected by a rotation of the rotary knob.

The present invention is based on the finding that by decoupling the piston from the actuation mechanism and by directly moving it via the spring mechanism, fast actuation of the actuation mechanism is now possible without causing excessive negative pressure in the sampling system, due to which otherwise, e.g., the vascular wall of a blood vessel in the patient might collapse, or degassing of the blood sampled from the patient might occur. Rather, by actuating the actuating mechanism, a spring mechanism is tensioned which causes, by releasing the tensioning energy in a slow and controlled manner, the piston to be lifted only at a moderate lifting speed and/or a lifting speed which is predefined accordingly and which results, e.g., in limited negative pressure for pulling the liquid and for sampling the patient's blood.

This results in the advantage that degassing of a liquid located in the line adjoining an opening of the reservoir, and of the blood sampled is avoided, and that as compared to conventional approaches, the risk of a vascular wall collapsing is clearly reduced.

The spring mechanism may be formed by a coil spring, which provides the advantage of a solution simple in design since a coil spring represents a simple and low-cost mechanical element easy to install.

The carrier bearing and/or the piston may be configured such that when the carrier bearing is displaced in a second direction, the carrier bearing engages with the piston so as to cause a displacement of the piston such that the volume of the fluid receiving reservoir is reduced. In this manner, a simple possibility of rapidly emptying the receiving container may be advantageously provided without requiring additional expenditure in terms of design.

The piston may comprise a piston rod provided with a piston disc, the spring mechanism being arranged between the piston disc and the carrier bearing. This offers the advantage of creating, by means of such an arrangement, a simple-design solution for tensioning the spring mechanism. By displacing the carrier bearing in a first direction, the spring mechanism between the carrier bearing and the piston rod is tensioned.

The actuation mechanism may comprise a rotary knob with a thread mechanism, the carrier bearing being provided at a thread element comprising a thread, the thread mechanism engaging into the thread of the thread element with mutual rotation protection, so that rotation of the rotary knob may cause the carrier bearing to be displaced. By means of such an arrangement of rotary knob, carrier bearing and thread element, a simple adjustment of a position may advantageously be achieved by a defined rotation of the rotary knob, which enables highly precise adjustment of a volume of the fluid reservoir.

The thread may have a high thread pitch, so that a maximum displacement in the carrier bearing can be caused by few revolutions, e.g. only one revolution, of the rotary knob. In this manner, the fluid handling device may be "pulled to be filled" fast without requiring a change in position of the operator's hands.

The thread element may comprise an internal bore, at the end of which the carrier bearing is formed; the piston with the piston disc projects into the end of the internal bore. This offers the advantage that the internal bore may serve as a guide for the piston.

The internal bore may be configured to act as a guide for the piston disc when the piston is displaced, the spring mechanism within the internal bore of the thread element being arranged between the carrier bearing and the piston disc. In this embodiment, the spring mechanism may be accommodated within the internal bore in a space-saving manner, whereby a large volume is available for fluid handling.

The internal bore may comprise a stage configured to ensure a minimum distance between the piston disc and the carrier bearing. This prevents tensioning of the spring mechanism beyond a predetermined amount while additionally enabling that filling of the receiving container by means of pulling and/or that displacing of the piston in the first direction may be immediately performed by the operator—by means of a force exerted upon the actuation mechanism—from that point in time when the spring mechanism is tensioned to a maximum and/or the stage engages with the piston disc, whereby reliable detachment of a piston plug from a container bottom provided with the container opening is ensured.

The piston may comprise a piston plug made of a reversibly deformable material, so that by means of a movement of the piston plug to a planar container bottom, fluid may be driven out of the fluid opening arranged in the planar container bottom, wherein the piston plug may comprise a recess in that surface which faces the planar container bottom, such that when the piston plug is pressed against the planar container bottom, a contact boundary line between the piston plug and the container bottom migrates toward the fluid opening under increasing pressure. This offers the advantage that the fluid reservoir may be fully emptied when the piston is pressed down. Alternatively, the piston may also comprise a conical piston plug.

Such a conical piston plug may comprise a reversibly deformable material; the container bottom may also have a conical shape, and a cone angle of the conical piston plug is larger than a cone angle of the conical container bottom. This, in turn, offers the advantage that a fluid reservoir may be completely emptied through a fluid opening located at the cone tip of the container bottom.

The actuation mechanism may be configured to tension the spring mechanism upon the piston in the receiving container being moved in a first direction of motion, and not to tension the spring mechanism upon the piston being moved in a second direction of motion opposite the first direction of motion. This ensures that the spring mechanism is relaxed when the piston is pressed down, which increases the service life of such a spring mechanism.

BRIEF DESCRIPTION OF THE DRAWINGS

Embodiments of the present invention will be detailed subsequently referring to the appended drawings, in which.

DETAILED DESCRIPTION OF THE INVENTION

In the following drawings, identical or similar elements are provided with identical or similar reference numerals, repeated descriptions of the reference numerals being omitted.

Figure 1A:
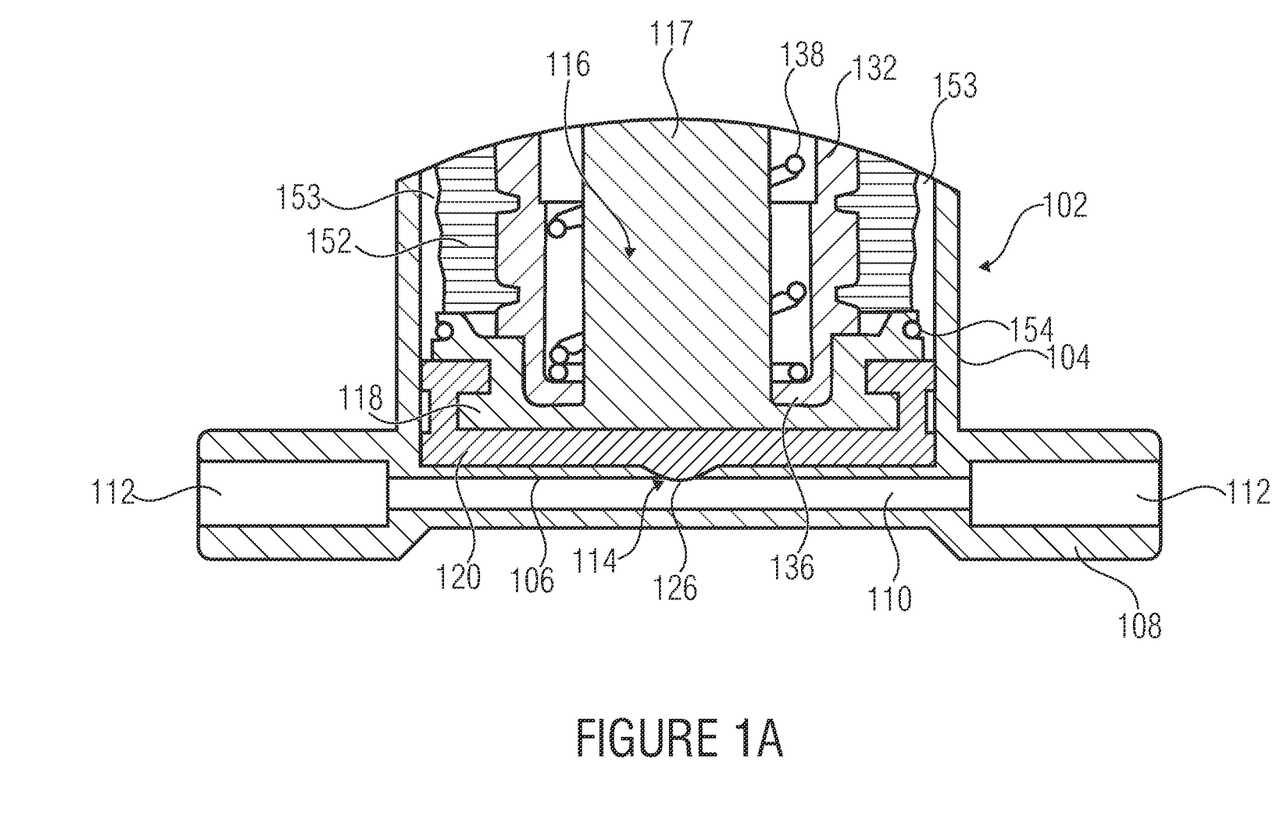
FIGS. 1A to 1D sectional side views of a fluid handling device at different points in time when it is being actuated in accordance with an embodiment of the present invention, FIG. 1A representing a detailed view only.

FIG. 1A shows a fluid handling device 100 in accordance with an embodiment of the present invention. Here, the fluid handling device 100 comprises a receiving container 102 having a side wall 104 as well as a planar (i.e. flat) container bottom 106. The receiving container 102 comprises a first portion 102a of cylindrical shape which adjoins the bottom 106 and is adjoined, in turn, by a second portion 102b of cylindrical shape which has a larger internal diameter. In addition, the receiving container 102 is attached to a connecting piece 108 comprising a flow channel 110 between two ports 112 of the connecting piece 108. A fluid opening 114 is centrally arranged, by way of example, in the flat container bottom 106 in such a manner that an exchange of fluid between the connecting channel 110 and the interior of the receiving container 102 is possible.

A piston 116 having a piston rod 117 and a piston plug support 118 arranged at the end of the piston rod 117 is arranged inside the receiving container 102, said piston 116 being movable in the longitudinal direction of the container 102, the piston plug support 118 having a slightly smaller diameter than the portion 102a and having an elastic, i.e. reversibly deformable, material arranged, as the piston plug 120, on its side which faces the bottom 106 as well as on its circumferential side, so that the piston plug 120 ensures fluid-tight sliding of the piston 116 along the inner wall of the container 102 and, thus, ensures that the fluid located within the container 102, such as infusion solution and/or mixed blood, for example, is ejected from the container 102 into the channel 110, and/or ensures that fluid is aspirated out of the channel 110.

In that surface of the piston plug which faces the container bottom 106, i.e. in the elastic material 120 of the piston plug, a recess 122, which in this case is annular by way of example, is arranged such that the recess initially comprises—starting from a side edge 124 of same as seen in the direction of the fluid opening 114—an increasing receiving depth, which decreases again in the area of a sealing plug 126 in the elastic material 120 arranged in the center of the piston plug, the sealing plug 126 being arranged opposite the fluid opening 114. In other words, the underside of the piston plug has a circular-symmetric concave shape. However, other shapes are also possible for the recess, such as a shape having a depth which is constant (in sections) and varies in a discontinuous manner, and a recess which has no sealing plug 126 and has, for example, a recess depth which monotonically increases from the edge to the center.

At an upper end of the piston 116, a piston disc 128 is arranged or attached to the piston, said piston disc 128 radially projecting from the piston rod 117 and enabling movable guidance of the piston 116 within a bore 130 of a thread element 132. The thread element 132 and the piston 116 are advantageously arranged in the receiving container 102 such that a relative rotation between the receiving container 102, on the one hand, and the thread element and optionally also the piston 116, on the other hand, does not take place. To this end, the thread element 132 comprises, in addition to the bore 130, an essentially cylindrical outer surface wherein an external thread 134 and here, by way of example, flat sections 135 are formed, so that the thread element 132 extends, in a manner in which it is protected from rotating, through a correspondingly shaped opening in a rotation protection disc 137, which itself, in turn, is arranged—in a manner in which it is protected from rotating and/or in a manner in which it is fixed to prevent rotation—at a boundary between the portions 102a and 102b in the container. The flat sections 135 can be seen in FIG. 1H. In addition, the thread element 132 includes, on the lower side, a flange 136 acting as a carrier bearing which projects inward in the direction of the piston 116 so as to form a bearing surface with a hole through which, in turn, the piston 116 extends.

A coil spring 138, which acts as a spring mechanism and here, in particular, as a compression spring, is arranged between the underside of the piston disc 128 and the top side of the flange 136 such that it surrounds the piston 116. In addition, the thread element 132 comprises a change in diameter within the bore 130 so as to be broader at the flange end than at the other end, whereby an annular support 140 is formed within the bore 130. The external diameter of the piston disc 128 is large enough so that the piston disc 128 can be located only in that part of the bore 130 which is located further apart from the flange 136, whereby excessive compression of the coil spring 138 is prevented, which will be addressed in more detail below.

In addition, the fluid handling device 100 comprises a rotary lid 142 attached to the receiving container 102 by means of a snap lock 144 so as to cover the opening of the container 102 from the top in the form of a vaulted rotary knob and to be rotatable, in relation to the container 102, about a common symmetry axis of the container 102 and the rotary lid 142. The rotary lid 142 comprises, on an inner surface of a vaulted outer handle part 145 of the rotary lid 142, a thread cylinder 146 which projects from said inner surface and comprises an internal thread which is formed on its inner surface and engages into the external thread 134, whereby a position and/or a height of the thread element 132, which is mounted such as to be protected against rotation, in the fluid handling device 100 may be adjusted by rotating the rotary lid 142.

The connection between the rotary lid 142 and the receiving container 102 comprises, e.g., a possibility of areation in the form of a gap 148 between the receiving container 102 and the rotary lid 142, so that an air exchange and, thus, equalization of pressure between an ambient pressure outside the fluid handling device 100 and an internal pressure within the fluid handling device 100 is possible. Alternatively, an opening having the same function might be provided in the rotary lid 142 or in the upper area of the container.

By means of a relative rotation between the thread mechanism 132 and the rotary lid 142, the thread element 132 is retractable and extendable within the thread cylinder 146. As was mentioned above, a rotation protection disc 137 is provided for this purpose which comprises a hole through which the thread element 132 extends and which is shaped such that the thread element 132 cannot rotate in relation to the disc 137. To complete the rotation protection in relation to the container 102, the disc 137, too, is arranged in the container 102 such as to be protected against rotation and/or inhibited from rotating. To this end, an upper sealing bead 150 of a sealing device 152 formed in the shape of an essentially cylindrical membrane having the shape of an accordion is clamped between an annular groove in an annular projection between the part 102a having the smaller diameter and the part 102b having the larger internal diameter of the container 102 and the rotation protection disc 137 in that, in the assembled state, that end of the projecting thread cylinder 146 which comprises a phase provided therein for centering purposes presses a portion, shaped accordingly and having the shape of a truncated cone, of the disc 137 downward against the sealing bead 150. By means of its friction, the sealing bead 150 of the membrane 152 ensures not only rotation protection of the disc 137 in relation to the container 102, but also ensures sealing, as will be described below.

The membrane 152 extends along the symmetry axis of the container from the transition between the container portions 102a and 102b up to the piston plug support 118 while surrounding the arrangement consisting of the piston 116 and the thread element 132, and separates, in a manner impermeable to germs and air—while forming pleats and undoing the formation thereof in the direction of the symmetry axis—an area 153 which is formed between a part of the internal wall 104 of the receiving container 102 which extends between the transition between the container portions 102a and 102b and the current position of the piston plug 120, and the membrane 152, from the remaining inner space, which is aerated in relation to the outside by, e.g., the slot 148, of the receiving container 102. To this end, the membrane 152 is attached at the top of the sealing bead 150 in a leak-proof manner, as was already mentioned. For attaching the membrane 152 to the piston plug support 118, the membrane 152 on this side also comprises, e.g., a sealing bead 154 formed in a circumferential manner, and is fitted, while being subject to slight tension, into a circumferential groove on an outer surface of the piston plug support 118. The membrane consists of a material impermeable to germs and air, which is impermeable to infectious material such as bacteria, viruses or germs, such as silicone, for example.

In the upper area, and/or the area remote from the bottom 106, of the portion 102a of the receiving container 102, an opening 156 is provided in the container wall 104 through which a gas exchange is facilitated, irrespective of the position of the piston 116, between the area 153 and an external environment of the fluid handling device 100. A filter 158 (e.g. a bacteria filter) may be provided in this opening 156 so as to prevent germs from entering the area 153 between the membrane 152 and the inner wall 104 of the receiving container from the external environment and from settling on the inner wall 104 of the housing, which might lead to contamination of the blood circulation connected to the channel 110 in the event that the temporarily stored fluid in the piston volume is expelled again.

In the following, the mode of operation of the inventive fluid handling device 100 is to be described in more detail. A basic state is to be initially assumed wherein the thread element 132 has the lowest state possible. This state is depicted in FIG. 1A. In this state, the thread element 132 is rotated out of the thread cylinder 146 to a maximum so as to contact that side of the piston plug support 118 which faces away from the container bottom 106 and so as to press, in this manner, the piston plug 122 against the bottom 106 with a force determined by the torque at the rotary lid 142 so that the piston plug lies flat against the bottom 106 in the relaxed unpressed state despite the recess 122, so that any liquid has been expelled from the inside of the plug into the channel 110, and so that the plug 126 ends flush with the inner wall of the channel 110, so that no dead-zone area and the associated accumulation of blood and germs arise within the channel. The spring 138 is in a slightly biased state, wherein the piston disc 128 is pressed against a position which is at a maximum distance from the flange 136 within the bore 130.

Figure 1B:
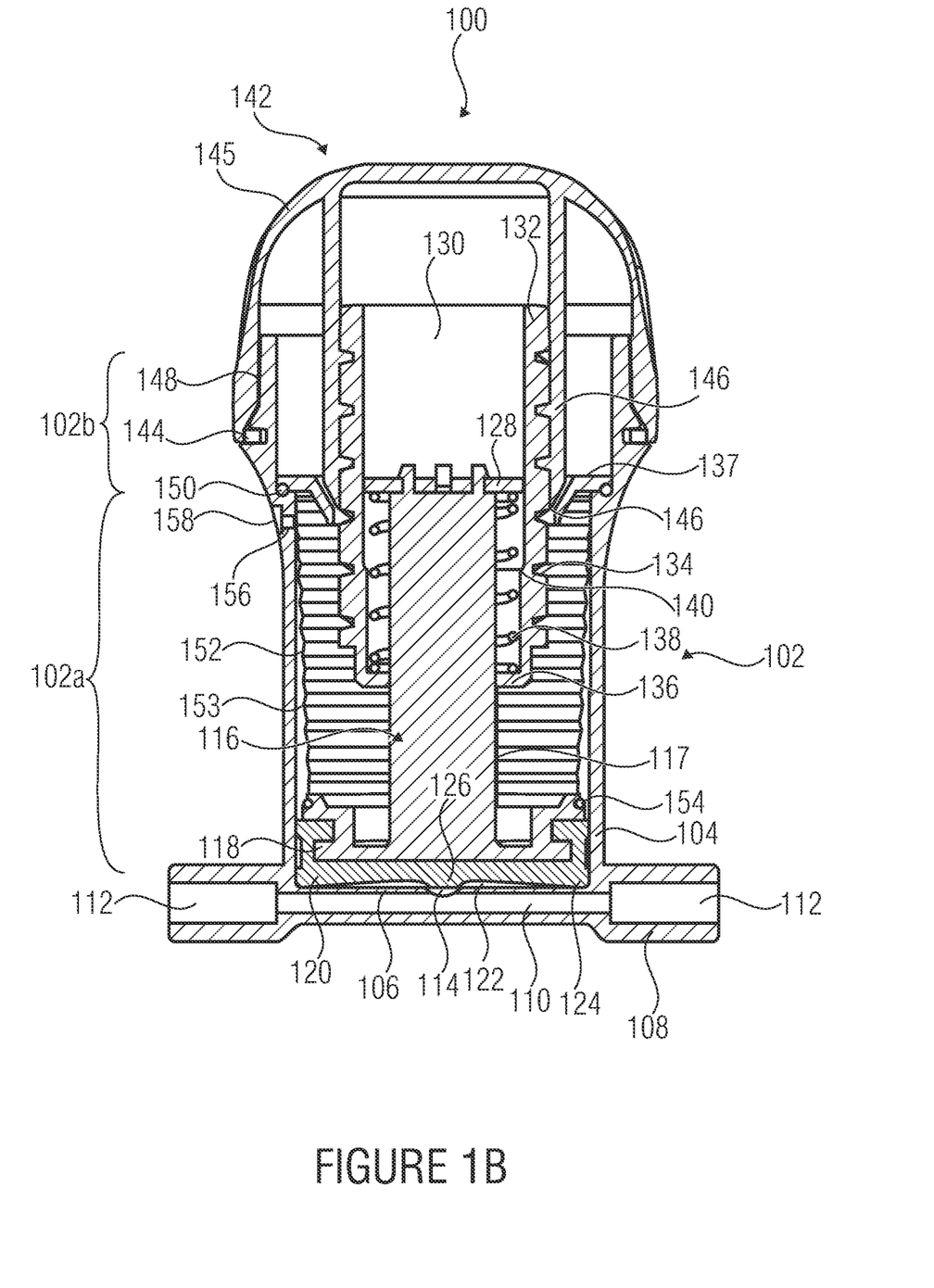

If the rotary lid 142 is rotated, the thread element 132 will be pulled upward as is depicted in FIG. 1B. In this manner, the spring 138 is initially compressed and tensioned further, which is caused by the flange 136 being lifted, since the piston 116 with the piston disc 128 initially cannot follow the upward movement of the thread element 132 and/or is not lifted with the same speed as the thread element 132 since, first of all, the piston plug 122 detaches itself from the bottom 106. Decoupling between the fast lifting of the thread element 132 and the slower lifting of the plug 116 by the coil spring 138 has the advantage that with a corresponding implementation of the external thread 134 of the thread element 132, in particular with a high thread pitch, the thread element 132 may be lifted by a very large amount by means of few revolutions or even only one revolution and/or by means of a short rotation path without simultaneously resulting in the piston 116 being "yanked up", whereby, as was already set forth, degassing of blood and/or a collapse of a blood vessel wall may be prevented. FIG. 1B shows a moment in time when the rotary lid 142 has just been rotated slightly and the thread element 132 has already been significantly, while the piston 116 has hardly moved yet.

Figure 1C:
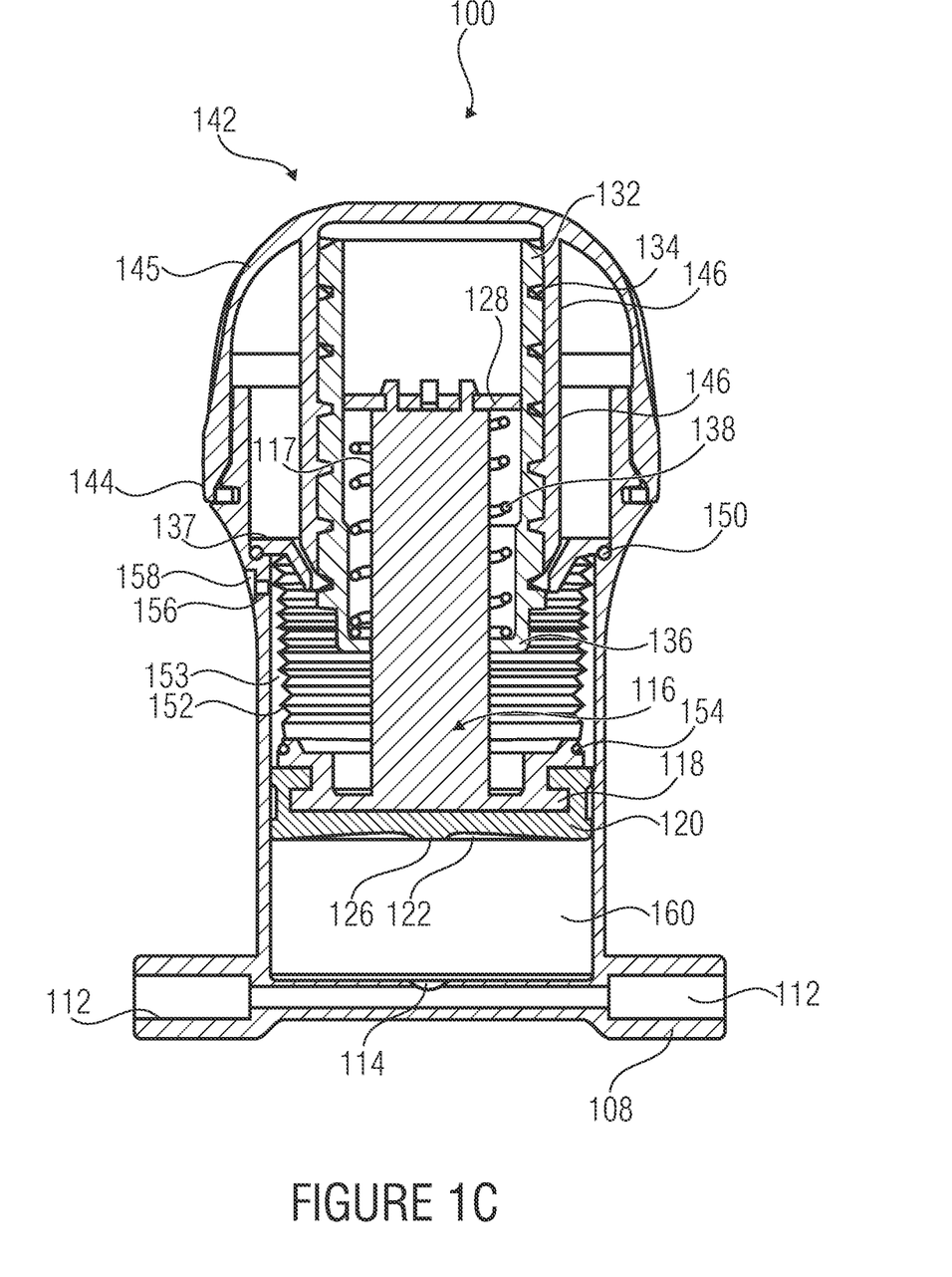

FIG. 1C represents a state wherein the thread element 132 has already been fully rotated upward, the piston plug 120 has detached itself from the bottom 106, and the piston 116 with the piston plug 120 is moving upward due to the force of the coil spring 138, so that liquid is aspirated into the piston chamber through the opening 114 from the channel 110. In particular, in FIG. 1C the piston plug 120 has already moved upward a certain distance, so that a fluid and/or liquid/mixed-blood reservoir has formed in the lower part of the receiving container 102. Here, it is also apparent that the membrane 152 may fold up in the manner of an accordion and thus follows a movement of the piston 116.

Before the further aspiration process is addressed, it shall be pointed out that there are various scenarios of how much the spring 138 is compressed between the states shown in FIGS. 1B and 1C. It is possible that the thread element 132 will come off the bottom, driven by the rotational movement of the rotary lid 142, so fast that the piston 116 will still be located near the starting position of FIGS. 1A and 1B, respectively, and so that, therefore, the support 140 will engage with the piston disc 128, so that, from this point onward, the upwardly directed force caused by the torque acting on the rotary lid 142, which acts upon the thread element 132, also acts directly on the piston 116. In this manner, reliable detachment of the piston plug 120 from the container bottom 106 is ensured since the detachment force is not limited to the maximum force of the compression spring 138, which is defined by the distance of the support 140 from the flange 136. On the other hand, the support 140 is arranged at such a position that the travel of the thread element from that point at which the support 140 may contact the piston disc 128 at the earliest (namely when the piston is located in the position of FIG. 1A) to the end position as is shown in FIG. 1C is short, so that during the interim period, during which the piston 116 moves at the same speed as the thread element 132, there is no risk of an excessive negative pressure within the piston volume and of the bubble formation associated therewith, and extends just as far as to ensure reliable detachment of the plug 122.

Figure 1D:
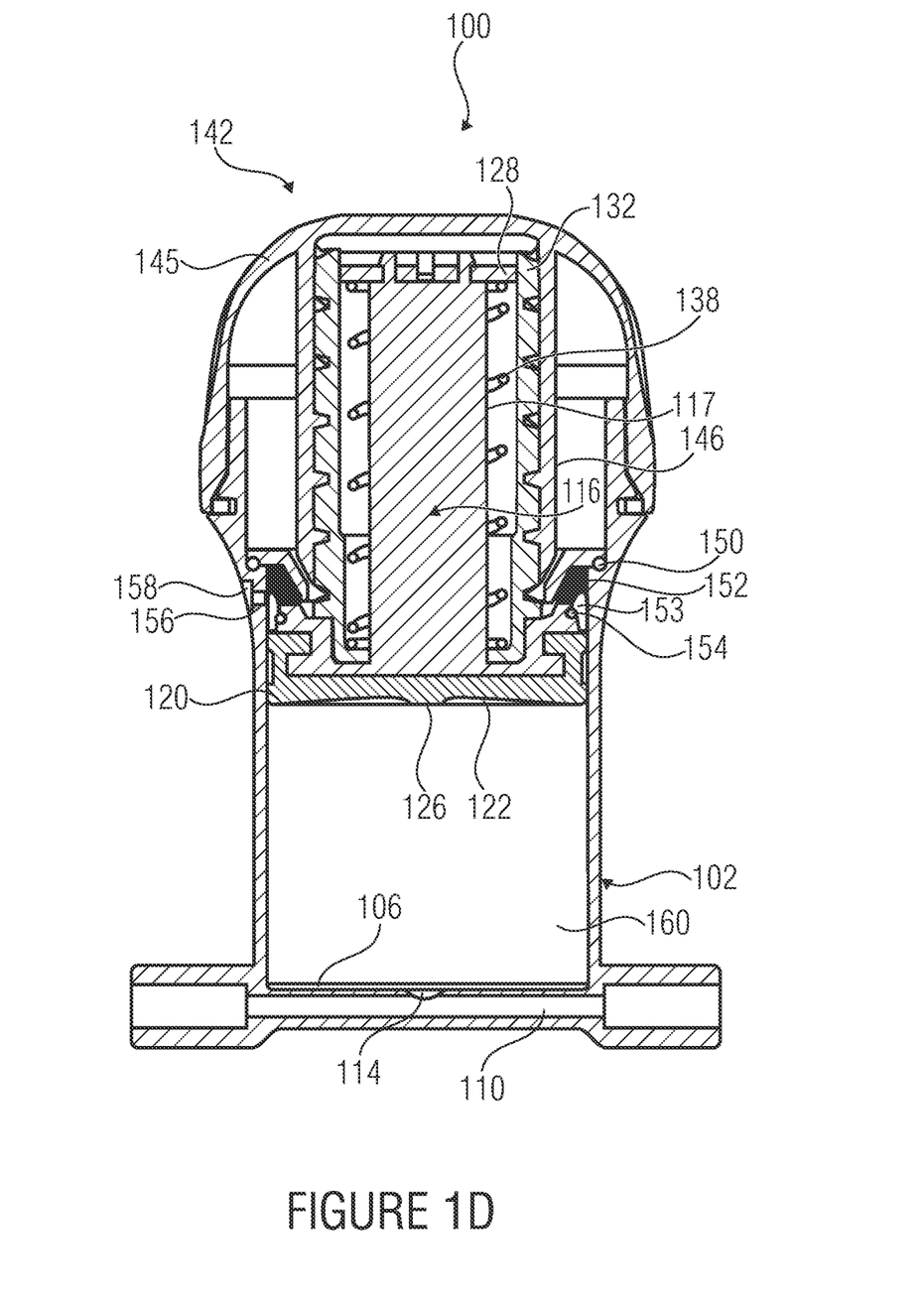

FIG. 1D shows the fluid handling device in a final state, i.e. when both the thread element 132 and the piston 116 are in positions of a maximum heights, so that the coil spring 138 is relaxed again (e.g. is biased at the predetermined bias). In this case, the membrane 152 is also folded up to a maximum extent, i.e. is embedded in the manner of an accordion in the area between the upper end of the piston plug 118 and the thread mechanism 146. Thus, in the state depicted in FIG. 1D, the blood reservoir 160 is at its maximum extension and/or its maximum filling volume. It is possible, in such a state, e.g., at a sampling device arranged between the channel 110 of the fluid handling device and the patient, to sample blood which is not mixed with infusion solution, so that there is no danger of the values of the analysis being distorted.

To keep a loss of liquid of the patient due to the blood sampling as low as possible, the blood located within the blood reservoir 160 during blood sampling may subsequently be recirculated to the patient. This may be effected in that the rotary lid 142 is rotated in the direction opposite to that used during "drawing up" of the fluid handling device, as a result of which the piston 116 is pressed down by the lower part of the flange 136 and/or of the thread element 132, and an overpressure results, which leads to the mixed blood which is found in the blood reservoir 160 being driven out into the flow channel 110 through the fluid opening 114. In this context, particular consideration of the pressure conditions is not highly critical, even though pressing down of the piston 136 by rotating the housing lid 142 should evidently be performed with care by the hospital personnel. However, a collapse of the vascular wall or degassing of the blood cannot occur in this case.

If the piston 116 with the piston plug 120 has been pressed down sufficiently when the blood was driven out by the thread element 132, an edge region of the reversibly deformable material 120 will first of all touch the planar housing bottom 106 on account of the recess 122. If the piston plug 118 is pressed down further, the elastic material 120 will be deformed such that the recess 122 will increasingly close and/or be reduced in size, specifically such that a contact boundary line which surrounds the fluid opening 114 and is located between the elastic material 120 and the planar container bottom 106 will migrate toward the fluid opening 114. In this manner it is ensured that the blood located within the fluid reservoir 160 is fully "pressed out" of the receiving container 102. In addition, once the blood reservoir 160 has been completely emptied, the fluid opening 114 may be closed by the sealing plug 126 in such a manner that it is advantageously absolutely flush with the inner wall of the channel, whereby coagulation due to a dead-zone area within the flow channel 110 may be avoided. As was described above, the sealing plug 126 is advantageously adapted to the shape of the fluid opening 114 so as to be flush with the inner wall of the channel.

Figure 1E:
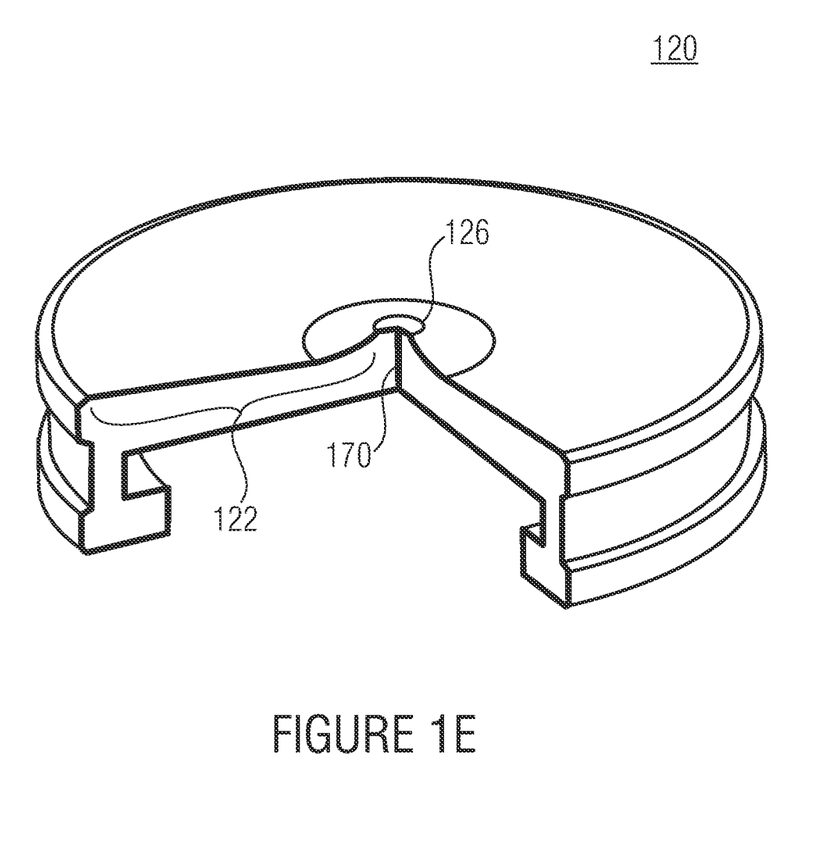
FIG. 1E a partial sectional spatial view of the piston plug of FIGS. 1A-1D.
Figure 1F:
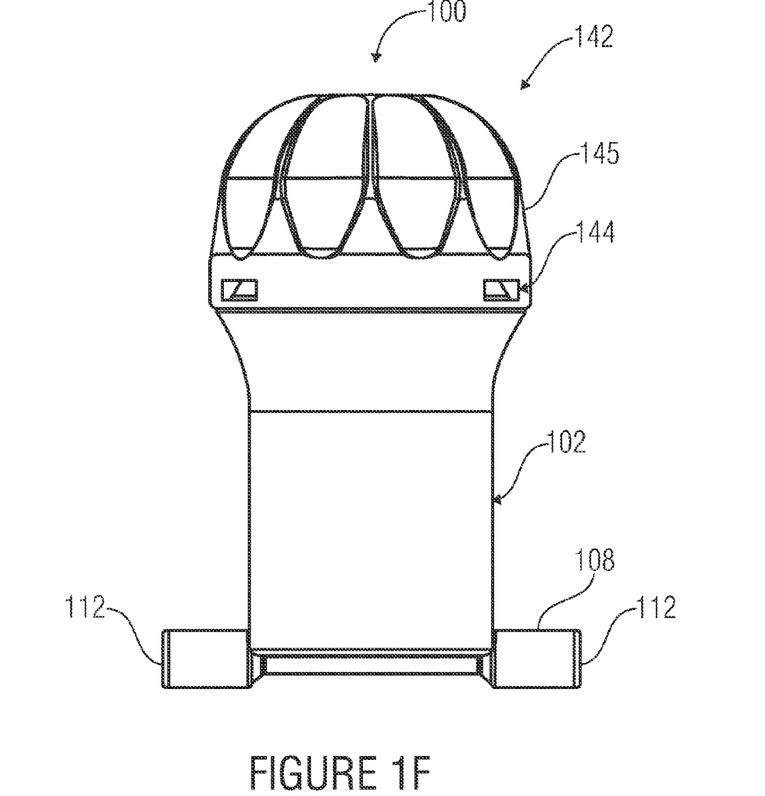
FIGS. 1F and G a top view and a side view, respectively, of the fluid handling device of FIGS. 1A-1D.
Figure 1G:
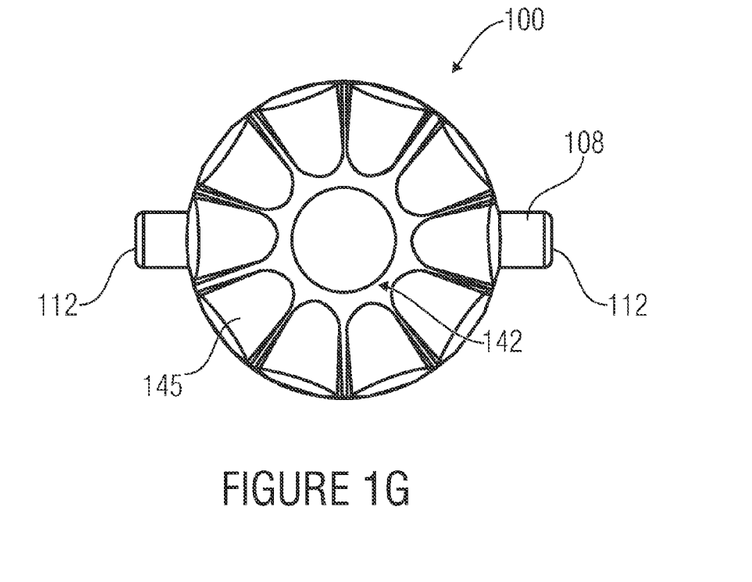
Figure 1H:
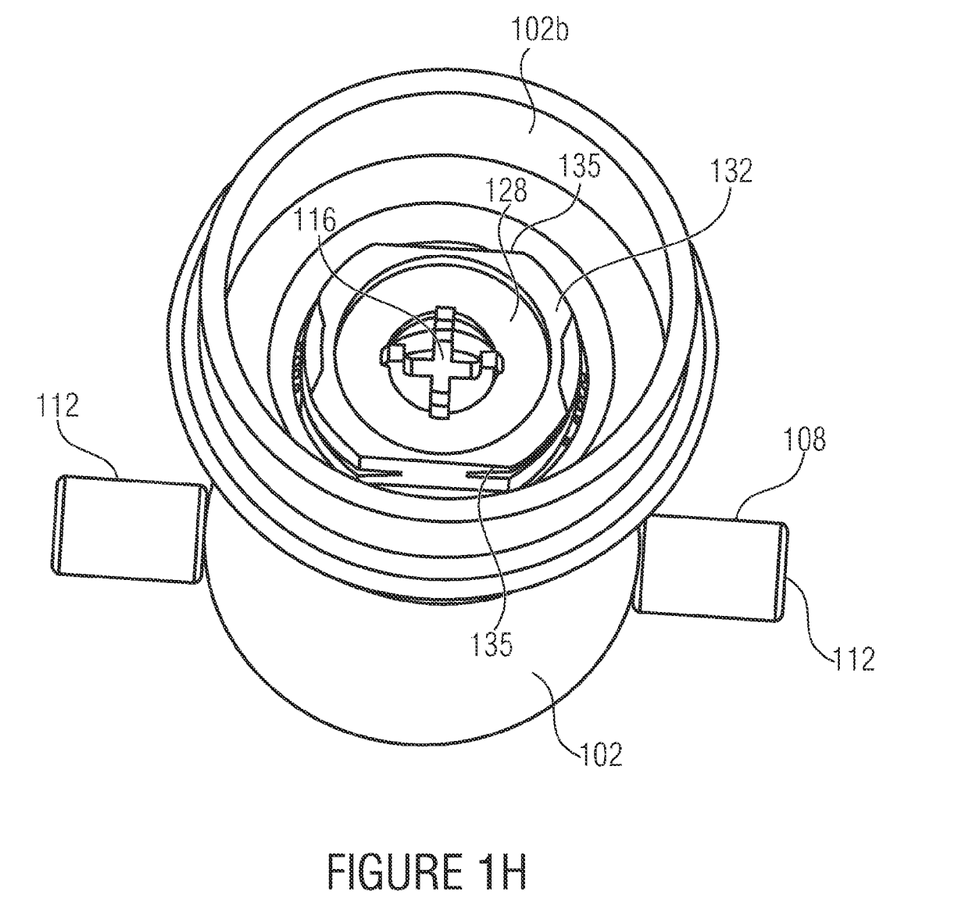
FIG. 1H a spatial view of the fluid handling device of FIGS. 1A-1D with the rotary lid removed.

In accordance with one embodiment, the recess 122 within the piston plug 120 may have a circular ring shape, as seen in a top view of the plug 120, about a center 170 defined by the fluid opening 114 and/or by the symmetry axis of, e.g., the container 102, as is depicted in FIG. 1E. Alternatively, the recess 122 might be arranged in an oval manner about the center 170. Accordingly, the fluid opening 114, too, may be circular or slit-shaped.

Once the blood has been fully pressed out of the receiving container 102, the fluid handling device is once again in a state as is depicted in FIG. 1A.

A gas exchange between the area 153, which is limited by the membrane 152 and the inner wall 104 of the container, and the outside is possible through the opening 156 in the lateral container wall 104, namely deaeration of the space 153 when the piston is moved upward, and aeration when the piston is moved downward; in the latter case, the filter 158 prevents germs from entering the space 153. The filter 158 may be a paper-like membrane, for example, which is attached, along its edge, to the housing 102 within the opening 120 by adhesives and/or glues, a welding seam or a retaining and/or clamping ring.

The possibility of aeration and deaeration via the opening 156 also offers an advantage when sterilizing the fluid handling device 100, such as once it has been assembled and inserted into a suitable packaging, such as an ETO gas-permeable packaging, since the space 153 may be evacuated in advance and then be filled with the ETO gas. Germs which have accumulated on the inner wall 104 of the container may thus be rendered harmless by being sterilized with a sterilization gas such as ETO, for example. By means of the bacteria filter 158, one can also prevent further germs from entering the area 153 between the membrane 152 and the inner wall 104 of the container when the fluid handling device 100 is utilized.

As compared to conventional approaches, such an arrangement of the opening 156, of the membrane 152 and of the bacteria filter 158 offers the advantage that a large bacteria filter, for example on the top side of the rotary lid, by means of which large-volume air exchange and, thus, equalization of pressure is facilitated upon actuation of the fluid handling device, is no longer required. Rather, a significantly smaller bacteria filter 158 may be used since a clearly smaller amount of gas volumes is to be exchanged.

It shall be mentioned merely for caution's sake that, in addition to the temporary storage of blood, the fluid handling device may also be used for handling other fluids or liquids as may be used, e.g., in chemistry and biochemistry; similar advantages may result here due to, e.g., the above-described avoidance of bubble formation, the complete emptying of the piston chamber and the capability of sterilization of the space 153 adjoining the inner surface of the piston chamber.

In summary, a fluid handling device has been described above which may be part, in particular as a blood reservoir, of a closed blood sampling system. The column of liquid is pulled back, via the reservoir, into a line coupled to the channel 110 until, e.g., pure blood can be sampled at a sampling site which is located along the line and is closer to the patient. Sampling may be effected via a sampling adapter through a puncture membrane. The pulled-back volume of liquid within the reservoir may subsequently be recirculated to the patient, so that a significant loss of liquid may be avoided in the event of frequent blood sampling. Since a closed blood-sampling system may be connected to a patient over a relatively long period of time (e.g. several days), it needs to be ensured that the interior of the system is not contaminated by introduction of germs. To this end, the above-mentioned membrane is mounted between the housing and the piston. During sterilization, which may take place in the assembled, or packaged state, ETO gas may reach, as an exemplary sterilization gas (ETO=ethylene oxide), the inner wall of the housing through the opening 156 and may subsequently be removed. The space between the housing and the membrane, however, is sterile even during utilization, which is ensured by the bacteria filter, which enables gas exchange but prevents migration of germs. The spring ensures that the piston plug is pulled back only at a speed ensuring that no degasification takes place in the liquid and/or that the vascular walls will not collapse as a result of an excessive negative pressure. In addition, this decoupling enables an optimized thread pitch between the rotary lid and the piston, so that the piston may be pulled right up to the stop with few rotations, e.g. only one rotation. A low pitch for limiting the pull-back speed of the piston is not required, so that even with relatively large volumes, handling remains practicable since the rotary lid need not be rotated very frequently.

The fluid handling device of FIGS. 1A-H is advantageous also from the point of view of manufacturing since assembly is a simple and fast process. In particular, during assembly, the piston 116 with the piston plug support 118 and the elastic material 120 attached thereto is initially inserted through the hole at the flange end of the thread element 132, and the spring 138 is introduced into the bore 130. While the spring 138 is compressed slightly, the piston disc 128 is then attached to that end of the piston 116 which is located opposite the piston plug support 118. Subsequently, the membrane 152 is attached to the piston plug support 118 by means of the sealing bead 154, here by means of a snap lock, by way of example (FIG. 1A). This arrangement is then inserted into the container 102, the sealing bead 150 being arranged in the transition area between the portions 102a and 102b of the container 102. Subsequently, the rotation protection disc is inserted into the portion 102b so as to rest upon the sealing bead 150. Finally, only the rotary lid 145 with its internal thread in the cylindrical projection 146 is coupled to the external thread in the thread element 132 and is then placed on top of the container 102 by means of the snap lock 144.

With regard to FIGS. 1A-H it shall be pointed out that, e.g., the membrane 152 need not be formed in the manner of an accordion. By exploiting the stretchability of the membrane material, the membrane 152 might also have only an essentially cylindrical shape in its relaxed state and might stretch downward only in the longitudinal direction upon movement of the piston plug 120. It would also be feasible to have a membrane 152 which does not stretch per se and which in a relaxed state has an essentially cylindrical shape with a length sufficient to extend, in the state shown in FIG. 1A, between the two sealing-bead attachment sites. However, providing the annular pleats in the membrane shown, which is formed in the manner of an accordion, offers the advantage that when the membrane 152 is expanded and compressed, the folding up and unfolding of the membrane 152 takes place in a systematic manner, so that the forces acting upon the piston 116 by means of the membrane 152 are easier to forecast.

In addition, it shall also be pointed out that even though the shape of the sealing plug 126 was not dealt with in detail above, the shapes of the sealing plug 126 and of the opening 114 advantageously match each other to such an extent that in the squeezed state shown in FIG. 1A, the sealing plug 126 is flush with the inner surface of the channel 110, as was described.

Finally, it shall be pointed out that the aeration opening 156 with the filter 158 need not necessarily be provided. For, first of all, the volume of the space 153 is small in the state shown in FIG. 1A, so that the volume may also be accommodated, even in the state shown in FIG. 1D, in the remaining upper space of the portion 102a below the rotation protection disc 137. And additionally, the membrane 153 may be formed of such a material, for example, that it seals off the space 153 in a germ-tight manner against the piston plug support 118 at normal operating temperatures, and allows, however, aeration/deaeration of the space 153 for sterilization purposes upon a change in temperature, such as an increase in temperature, for example. It would also be feasible for the sealing bead 154 to have precisely such an amount of tension during attachment to the piston plug support 118 that a gas exchange is possible in a vacuum environment during sterilization, but germ-tightness is nevertheless ensured during normal use. In the latter case, the membrane might be formed to be somewhat stiffer in the vicinity of the sealing bead 154, so that upon formation of an inward bulge upon application of the vacuum, it is pressed about an edge provided in the support 118, so that the sealing bead 154 loosens its fit within a corresponding groove in the support 118.

An embodiment of a fluid handling device was described above wherein the piston volume provided for temporary storage of fluid was provided externally of the channel 110 from which the fluid that was to be temporarily stored was to be sampled through the fluid opening 114. In the emptied state shown in FIG. 1A, the fluid opening 114 had been closed such that the channel 110 essentially comprised an inner wall as if the fluid handling opening was not there. In the following, a different embodiment will be described with reference to FIG. 2, wherein the inside of the reservoir acts as part of the flow channel, i.e. wherein a gap will remain, independently of the position of the piston, between the container bottom and the piston, via which gap two openings which are provided in the container bottom and which are adjoined, in turn, by the further channel, communicate with each other.

Figure 2:
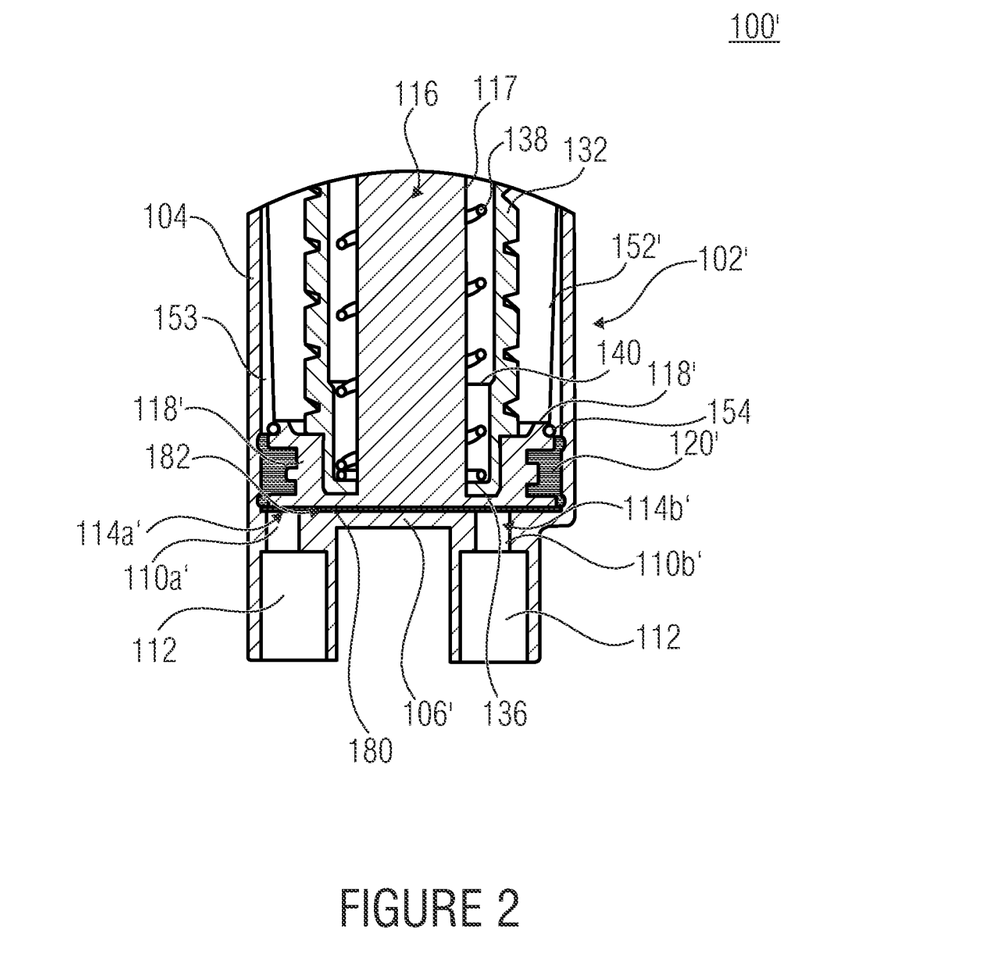
FIG. 2 a sectional view of a fluid handling device in accordance with a further embodiment of the present invention in a position which corresponds to that of FIG. 1A.

The embodiment of FIG. 2 will be described in more detail below. The fluid handling container of FIG. 2 is generally provided with the reference numeral 100' and in many parts matches the fluid handling device 100 of FIGS. 1A-H. To simplify the description, therefore, such components which are identical to those of FIGS. 1A-H are provided with the same reference numerals in FIG. 2, whereas such elements which are only similar in function to those of FIGS. 1A-H but are configured in a slightly different manner comprise similar reference numerals but are provided with an apostrophe in each case.

FIG. 2 shows the fluid handling container 100' in a piston position corresponding to that of FIG. 1A. Consequently, the piston 116 is in the lower position, pressed down by the lower end of the thread element 132, which acts directly upon the piston plug support and/or the piston plug 118'. FIG. 2 shows only a detailed view of the fluid handling device 100' since said device matches that of FIGS. 1A-H, e.g., with regard to the rotary lid, the thread element 132, the opening 156 with the filter 158, and the rotation protection disc 137. As another example of the membrane, FIG. 2 shows a stretchable, smooth, essentially cylinder-shaped membrane 152' which, in the state shown in FIG. 2, is in a state of maximum tension and is clamped between the upper sealing bead 150 (FIG. 1B) and a lower sealing bead 154, the latter in turn being seated, when under tension, in a corresponding circumferential groove in the piston plug support 118' so as to seal the space 153 off in a germ-tight manner against the interior of the housing which communicates with the outside. Unlike the embodiment of FIGS. 1A-H, the housing bottom 106' comprises two fluid openings 114a' and 114b', which in the embodiment of FIG. 2 are arranged closer to the edge of the bottom 106', by way of example; however, an arrangement where one of the openings 114a' and 114b' is located at the center is also possible. In addition, the openings 114a' and 114b' here are arranged, by way of example, on different radii with regard to the center of the bottom; for example, that opening which is spaced further apart from the center acts as an entrance and/or is provided for being arranged in a proximal manner, whereas the other one acts as an exit and/or is provided for being arranged in a distal manner. Arranging both openings on the same radius is also possible, however. It is also feasible to arrange the bores as is done in FIG. 1A, it being possible for the central axes of the ports 112 not to extend in parallel with the central axis of the receiving container 102', but, for example, perpendicularly in relation thereto and, for example, at the level of the housing bottom 106' or slightly above same (the latter alternative is not shown).

Unlike the embodiment of FIGS. 1A-H, the piston plug support 118' is not provided with the elastic piston plug material 120', on the side facing the bottom 106', in a closed area of same which is located opposite both fluid openings 114a' and 114b'. Rather, in FIG. 2, said elastic piston plug material 120' is provided, by way of example, only on that external circumferential edge, at the piston plug support 118', which faces the inner wall 104 so as to form a ring seal and to enable fluid-tight expulsion of fluid from the stroke volume by the piston plug support 118'.

This means that, unlike the embodiment of FIGS. 1A-H, the reservoir volume is not adjoined by any elastic material but by the rigid or hard material of the piston 116 itself. The elasticity property enabling complete emptying is not necessary in the embodiment of FIG. 2 since in said embodiment, a fluidic communication between both fluid openings 114a' and 114b' is to be constantly maintained. To ensure this, small projecting spacers 180 are provided, in the present case, on that side of the bottom 106' which faces the piston 116, for example, said spacers 180 ensuring that even when the piston 116 is at its lowest position, a gap 182 is maintained between the piston 116 and the bottom 106', via which gap 182 the fluid openings 114a' and 114b' are in fluidic communication with each other. Alternatively or additionally, the spacers 180 might obviously also be provided on that side of the piston plug support 118' which faces the bottom 106'.

Moreover, the container 102' is shaped such that the fluid openings 114a' and 114b' are each adjoined by a portion 110a' and 110b', respectively, of the flow channel, a port 112 being provided, respectively, at the ends of same which are located opposite the openings 114a, b'.

Now that the structure of the fluid handling device 100' has been described above, reference shall be made, with regard to its mode of operation, to the above description relating to the device 100, at least as far as the piston movement and the aspiration and ejection processes are concerned, the difference being that in this case two fluid openings 114a' and 114b' are provided instead of only one. However, with the device 100', there is constantly a fluidic communication between the two ports 112, or through the channel 110a', 110b' and the gap 182. Even in the embodiment of FIG. 2, therefore, mixed blood may be temporarily stored within the reservoir volume, such as in an arrangement wherein the device 100' is connected into a pressure measurement line, so that, e.g., the channel portion 110b' faces the patient, and the channel portion 110a' faces the pressure sensor. In the temporarily stored state of the device 100', blood might then be sampled at a sampling site arranged closer to the patient, whereupon the temporarily stored blood might be recirculated to the pressure measurement line.

An advantage of the arrangement of FIG. 2 as compared to that of FIGS. 1A-H consists only in that in the case of FIG. 2, no elastic material 120' borders on the liquid within the pressure measurement line and, in particular, on the liquid within the reservoir volume, or elastic material 120' borders on said liquid only across a very small adjacent surface area, so that pressure measurement with respect to the liquid is not influenced by said elastic material and/or so that, in more precise terms, pressure changes are not attenuated by the elastic material. In FIG. 2, rather, the rigid piston 116 itself borders on the reservoir volume.

Due to the fact that a gap is maintained between the piston and the container bottom, it is not possible to completely press out the temporarily stored liquid, such as mixed blood, for example, from the reservoir volume; however, this does not lead to problems in terms of coagulation or the like in this case since even in the normal case of the piston being pressed down, a flow through the gap is maintained which flushes out residual blood and the like from inside the reservoir.

Finally, it shall also be pointed out merely for caution's sake that the possibilities of modification that were explicitly mentioned with reference to the embodiment of FIGS. 1A-H may obviously also be transferred to the embodiment of FIG. 2 as long as they do not conflict with the above description of FIG. 2.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A fluid handling device comprising:
a receiving container with a piston arranged therein in a displaceable manner, such that a volume of a fluid receiving reservoir may be changed by a displacement of the piston;
an actuation mechanism configured to displace a carrier bearing upon actuation of the former; and
a spring mechanism configured to transfer a force from the carrier bearing to the piston so as to effect, in response to a displacement of the carrier bearing in a first direction, a displacement of the piston within the receiving container such that the volume of the fluid receiving reservoir is increased,
wherein the spring mechanism is a compression spring that is configured to be compressed due to a displacement of the carrier bearing in the first direction,
the actuation mechanism comprising a rotary knob with a thread mechanism, the carrier bearing being mounted on a thread element comprising a thread, the thread mechanism engaging with the thread of the thread element so that the displacement of the carrier bearing may be effected by a rotation of the rotary knob.

2. The fluid handling device as claimed in claim 1, wherein the spring mechanism is a coil spring or a gas spring.

3. The fluid handling device as claimed in claim 1, wherein the carrier bearing and the piston are configured such that, upon a displacement of the carrier bearing in a second direction, the carrier bearing engages with the piston so as to effect a displacement of the piston such that the volume of the fluid receiving reservoir is reduced.

4. The fluid handling device as claimed in claim 1, wherein the piston comprises a piston rod provided with a piston disc, the spring mechanism being arranged between the piston disc and the carrier bearing.

5. The fluid handling device as claimed in claim 1, wherein the thread comprises a thread pitch such that a maximum displacement of the carrier bearing can be effected by one revolution of the rotary knob or less.

6. The fluid handling device as claimed in claim 4, wherein the thread element comprises an internal bore at the end of which the carrier bearing is formed, the piston and the piston disc projecting into the internal bore.

7. The fluid handling device as claimed in claim 6, wherein the internal bore is configured to act as a guide of the piston disc upon displacement of the piston, the spring mechanism being arranged within the internal bore of the thread element, between the carrier bearing and the piston disc.

8. The fluid handling device as claimed in claim 7, wherein the internal bore comprises a stage configured to ensure a minimum distance between the piston disc and the carrier bearing and to enable direct transfer of forces from the thread element to the piston in the event of a movement of the thread element in the first direction.

9. The fluid handling device as claimed in claim 1, wherein the piston comprises a piston plug comprising a reversibly deformable material, it being possible for fluid to be driven out of a fluid opening arranged in a planar container bottom by a movement of the piston plug to said planar container bottom, the piston plug comprising a recess in that surface which faces the planar container bottom, such that when the piston plug is pressed against the planar container bottom, a contact boundary line between the piston plug and the container bottom migrates toward the fluid opening as pressure increases.

10. The fluid handling device as claimed in claim 1, wherein the receiving container comprises a container bottom with two fluid openings, a spacer being arranged on a side of the piston which faces the bottom and/or on a side of the bottom which faces the piston so as enable fluidic communication between the two fluid openings independently of a position of the piston.

11. The fluid handling device as claimed in claim 1, wherein the piston with a piston plug is arranged within the receiving container in such a manner that the fluid receiving reservoir is formed between the piston plug, a wall of the receiving container and a container bottom of the receiving container which has a fluid opening formed therein, the fluid handling device further comprising a seal attached to the receiving container and to the piston so as to shield off in a gas-tight manner a first area of the receiving container adjacent to a portion of the wall of the receiving container across which the piston plug of the piston may be displaced, from a second area of the receiving container which surrounds the piston.

12. The fluid handling device as claimed in claim 11, further comprising:
    an opening in the wall which is in fluidic communication with the first area and is arranged externally to that portion of the wall across which the piston plug of the piston may be displaced, for aerating and deaerating the first area.

13. The fluid handling device as claimed in claim 12, a filter being arranged in the opening in the wall or at the opening in the wall so as to prevent germs from entering the first area during aeration of the first area.

14. The fluid handling device as claimed in claim 13, wherein the filter is configured to prevent biological, infectious material, in particular bacteria, viruses and germs, from entering.

15. The fluid handling device as claimed in claim 11, wherein the seal is configured to fold up and unfold upon a movement of the piston.

16. The fluid handling device of claim 1, wherein the spring mechanism surrounds the piston.

* * * * *